United States Patent [19]

Harnoncourt et al.

[11] Patent Number: 5,645,071
[45] Date of Patent: Jul. 8, 1997

[54] METHOD FOR THE MEASUREMENT OF THE MOLAR MASS OF GASES OR GAS MIXTURES AND AN APPARATUS FOR THE PERFORMANCE OF THE METHOD

[75] Inventors: Karl Harnoncourt; Dieter Patzold, both of Graz, Austria; Walter Guggenbuhl, Stäfe; Christian Buess, Zürich, both of Switzerland

[73] Assignee: NDD Medizintechnik GmbH, Wurzburg, Germany

[21] Appl. No.: 379,465

[22] PCT Filed: May 19, 1994

[86] PCT No.: PCT/EP94/01629

§ 371 Date: Apr. 12, 1995

§ 102(e) Date: Apr. 12, 1995

[87] PCT Pub. No.: WO94/28790

PCT Pub. Date: Dec. 22, 1994

[30] Foreign Application Priority Data

Jun. 4, 1993 [DE] Germany ............... 43 18 690.4

[51] Int. Cl.⁶ ................................................ A61B 5/08
[52] U.S. Cl. ........................... 128/719; 73/861.28
[58] Field of Search ........................ 128/716, 729, 128/660.01, 660.02, 661.07; 73/861.28

[56] References Cited

U.S. PATENT DOCUMENTS

| | | | |
|---|---|---|---|
| 4,425,805 | 1/1984 | Ogura et al. | 73/861.29 |
| 4,545,244 | 10/1985 | Yasuda et al. | 73/861.29 |
| 4,581,942 | 4/1986 | Ogura et al. | 128/719 |
| 4,850,371 | 7/1989 | Broadhurst et al. | 128/719 |
| 4,914,959 | 4/1990 | Mylvaganam et al. | 73/861.28 |

FOREIGN PATENT DOCUMENTS

| | | |
|---|---|---|
| 0017162 | 10/1980 | European Pat. Off. . |
| 60-117149 | 6/1985 | Japan . |
| 60-181616 | 9/1985 | Japan . |
| 669463 | 3/1989 | Switzerland . |
| 9202177 | 2/1992 | WIPO . |

OTHER PUBLICATIONS

Buess et al., "Design and Construction of a Pulsed Ultrasonic Air Flowmeter," IEEE Transactions on Biomedical Engineering, vol. BME–33(8), pp. 768–774. Aug. 1986.
Buess et al., "Ultrasonic Respiration Analysis," Proceedings of the Annual International Conference of the IEEE Engineering in Medicine and Biology Society, vol. 13, No. 4, pp. 1597–1598. Oct. 1991.

Primary Examiner—Lee S. Cohen
Assistant Examiner—Eric F. Winakur
Attorney, Agent, or Firm—Keck, Mahin & Cate

[57] ABSTRACT

The invention relates to a method for the measurement of the molar mass of a gas or gas mixture and an apparatus for the performance of the method. The gas or gas mixture to be investigated is passed through at least one holder, on which at least one sonic or ultrasonic transmit-receive cell is arranged defining a baseline and preferably arranged obliquely to the axis of the tube. The sonic or ultrasonic transmit-receive elements radiate a pulsed sonic signal, which measures the transit times of the sonic pulses along the baseline. Using a temperature probe for instance the variations in gas temperature along the at least one sonic transmission path is determined. From the transit time of the sonic pulses and the measured or assumed temperature the molar mass is found. The apparatus in accordance with the invention may be employed with advantage in pulmonary function diagnostics.

29 Claims, 3 Drawing Sheets

5,645,071

METHOD FOR THE MEASUREMENT OF THE MOLAR MASS OF GASES OR GAS MIXTURES AND AN APPARATUS FOR THE PERFORMANCE OF THE METHOD

FIELD OF THE INVENTION

The invention relates to a method for the measurement of the molecular mass of gases or mixtures of gases and to an apparatus for the performance of the method.

BACKGROUND OF THE INVENTION

For the determination of the composition of gases or gas mixtures mass spectrometers or gas specific sensors are generally employed. Mass spectrometers are complex instruments, which permit extremely accurate gas analysis. Sensors for measurement of the concentration of specific gases are on the contrary normally simpler devices, which calculate the concentration of a given gas on the basis of certain physical or chemical properties thereof, as for example an absorption line in its spectrum or a paramagnetic property of the gas.

SUMMARY OF THE INVENTION

One object of the invention is to determine the molecular mass of a gas or gas mixture in a free holder cross section, that is to say without any interference in the flow geometry.

In accordance with the invention this object is to be attained by passing the gas to be investigated through at least one holder, on which at least one sonic or, respectively, ultrasonic transmit and receive cell is arranged as a baseline and preferably obliquely to the tube axis. The sonic or, respectively, ultrasonic transmit and receive cells radiate a pulsed sonic signal. The transit times of the sonic pulses along the baseline are measured. The temperature may be estimated. Using at least one temperature probe it is however possible for the variations in gas temperature to be measured as well for at least one sonic transmission baseline. The molar mass is found from the transit time of the sonic pulses and from the temperature.

Ultrasonic sensors, as applied in the present invention, are generally known in the fields of ultrasonic spirometry in connection with another purpose. For instance in the Japanese patent publication 60-117149 A and the Swiss patent publication 669,463 A5 ultrasonic spirometers are disclosed, in the case of which a transmit-receive cell pair is arranged on a baseline obliquely in relation to the axis of the instrument's duct. In the case of such known ultrasonic spirometers the flow velocity is determined using ultrasonic transit time measurement.

This inherently known effect may in accordance with claim 8 be utilized in the method in accordance with the invention since the transit times of the sonic pulses are also employed for the calculation of the flow velocities of the gas or gas mixture, whose molar mass is determined. In this respect linearity errors in the computation of the flow velocity may be corrected in an advantageous fashion by using an electronic circuit at the output.

The above mentioned method in accordance with the invention may be more particularly used in pulmonary function diagnostics, since in this case both the results of the flow measurement and also those of continuous gas analysis are of interest.

In the case of pulmonary function diagnostics as so far practiced gas analyses have been performed by means of a plurality of sensors which are specific for the respective gas components. As a rule measurement by such sensors is in a shunted flow, that is to say part of the flow is branched off from the gas composition to be measured and subjected to measurement using such sensors. These known methods of measurement are complex and, owing to the necessary tapping of part of the gas flow, also lead to spurious results. By means of the method in accordance with the invention, pulmonary function analysis may be performed in real time and on-line. The measurements may then be performed using one ultrasonic sensor and only one additional sensor, something representing a saving in apparatus complexity. More particularly, it is possible for the method to be employed to determine the following parameters in a simple fashion:

The lung volume including FRC, the $N_2$ wash-out curve or, respectively, the helium wash-in curve, the molar mass profile of the expiratory alveolar gas curve. Owing to the above mentioned combination of an ultrasonic sensor with a further gas sensor it is possible to also determine oxygen uptake and $CO_2$ release and the respiratory coefficient (V $CO_2$/$VO_2$)

Furthermore using continuous measurements of the molar mass it is possible, provided same are simultaneously combined with volume measurement, to determine the aerobic/anaerobic threshold during oxygen uptake in order for instance to monitor training effects.

An apparatus for the performance of the method in accordance with the invention comprises at least one sonic or, respectively, ultrasonic transmit-receive cell, which is also set obliquely in relation to the axis of the holder.

Furthermore at least one temperature probe may be placed along the at least one baseline so defined. The openings, directed into the instrument's duct, of the chambers, in which the sonic or, respectively, ultrasonic transmit-receive cells are respectively arranged, may be shut off by sonically transparent gauze in order to avoid eddies in the gas flow.

In the holder it is also possible for an interchangeable plug-in respiratory tube to be inserted, which at the transition to the baseline comprises calibrated windows of such a type that inserts may be placed in the corresponding openings which inserts are transparent for sonic waves but substantially prevent access of germs and dirt. This principle has also been disclosed in the non-prior published German patent application P 42 22 286. Owing to the provision of the interchangeable respiratory tube there is the possibility of completely hygienic spirometry.

In order to avoid the interfering effect of sonic reflection in the sonic duct it is possible to provide damping elements, it being preferred to provide a sonically absorbing surface on tube constituting the holder or, respectively, the interchangeable respiratory tube.

Moreover it is possible to provide elements at the flow inlets and, respectively, outlets in order to cause eddying of gas or gas mixture flowing and out.

In order to set a predetermined temperature and to prevent condensation a heating means may be additionally provided in the apparatus.

Besides the tube constituting the holder it is possible in accordance with an advantageously compact design to have cavities in order to accommodate electronic circuit components. Further advantageous embodiments of the invention will be gathered from the dependent claims.

The invention furthermore relates to an apparatus for the determination of the functional residual volume (FRC) of the lung in pulmonary function diagnostics and preferably possesses preferred features of the above described apparatus. In the case of this apparatus in accordance with the invention a connecting adapter may be mounted on the holder or the respiratory tube, such adapter having a branch tube, at whose one end a low-inertia bag is able to be mounted and is able to be charged with $O_2$ or a gas mixture. At the end of the branch tube, on which the bag is mounted, a inspiration valve is arranged. At the other, free end of the branch tube a expiration valve is arranged.

In accordance with one possible embodiment of this apparatus in accordance with the invention the branch tube is made integrally with the readily interchangeable respiratory tube. In accordance with another embodiment, the branch tube is adapted to be connected with the inserted valve by way of a docking mechanism with the respiratory tube or the readily interchanged respiratory tube. A charging port can be provided on the low-inertia bag for filling with the gas to be inhaled. In this design there is a device for connection with an extraneous gas, which may be mounted directly on the holder or on the readily interchanged respiratory tube. Using suitable software, the gas inlet and, respectively, gas flushing volumes may be applied from the density and flow parameters for the determination of the functional residual volume of the lungs. The connecting adapter is in this case so designed that during an expiration phase it so docks on a gas container, i.e. the low-inertia bag, that inhalation after this takes place from such gas container, whereas expired gas is conducted away to the outside. Owing to the provision of the two valves it is now possible to ensure that inhalation through contaminated parts impossible. The additional part of the above explained apparatus may if desired be designed to be disposable. The software for the simultaneous evaluation of the flow and density signals may take into account all effects resulting from the gas temperature, gas humidity and mass of the gas components. The calculation of the functional residual volume (FRC) of the lungs is for example performed using the familiar rules for $N_2$ flushing method or in accordance with analogous methods.

A still further design in accordance with the invention relates to an apparatus for the measurement of the molar mass of a gas or gas mixture for the determination of various different exhalation parameters in pulmonary function diagnostics, which preferably comprises features of the above mentioned forms of the invention, in the case of which in addition to the sonic or, respectively, ultrasonic transmit and/or receive cell pair either a $CO_2$ sensor on an infrared basis or an $O_2$ is provided.

Given an integrated form of the $CO_2$ sensor, simultaneous on-line infrared analysis for $CO_2$ becomes possible in hygienic ultrasonic spirometry. Hygienic spirometry involves the use of the readily interchangeable respiratory tubes. In this case, in accordance with an advantageous design of the invention, two optically transparent windows are provided at point, at which the infrared light source and the infrared sensor are arranged.

Alternatively to this, it is possible for the infrared light source and the infrared sensor to be arranged in the housing at a given position in parallel. In this case only one window is provided in the holder, which is arranged opposite to a mirror.

When an integrated $O_2$ is provided it is possible for an opening to be provided in the readily interchangeable internal tube, which is able to be inserted into the holder, such opening being shut off by a thin $O_2$ permeable but opaque diaphragm, a fluorescence indicator sensitive to $O_2$ being provided on the outside. When the respiratory tube is inserted there is at a corresponding position on the apparatus, i.e. within the spirometer head, a hole, which may be fitted with an optical connection (for example a fiber optics connection) for the optical system. This latter may in a known fashion comprise a light source for the exciting light and a sensor for the signal pulses.

For each of the above mentioned possible designs electronic evaluation is provided for, such evaluation taking into account temperature and humidity effects and being designed to derive conventional spiro-ergometry data from the mass and gas signal in combination with spirometric data, which are derived from the flow signals.

For humidity measurement it is possible to integrate additional measuring feelers in the apparatus.

BRIEF DESCRIPTION OF THE DRAWINGS

Further advantageous developments and convenient forms of the invention will be understood from the following detailed descriptive disclosure of embodiments thereof in conjunction with the accompanying drawings.

DETAILED DESCRIPTION OF THE PREFERRED EMBODIMENTS

Figure 1:
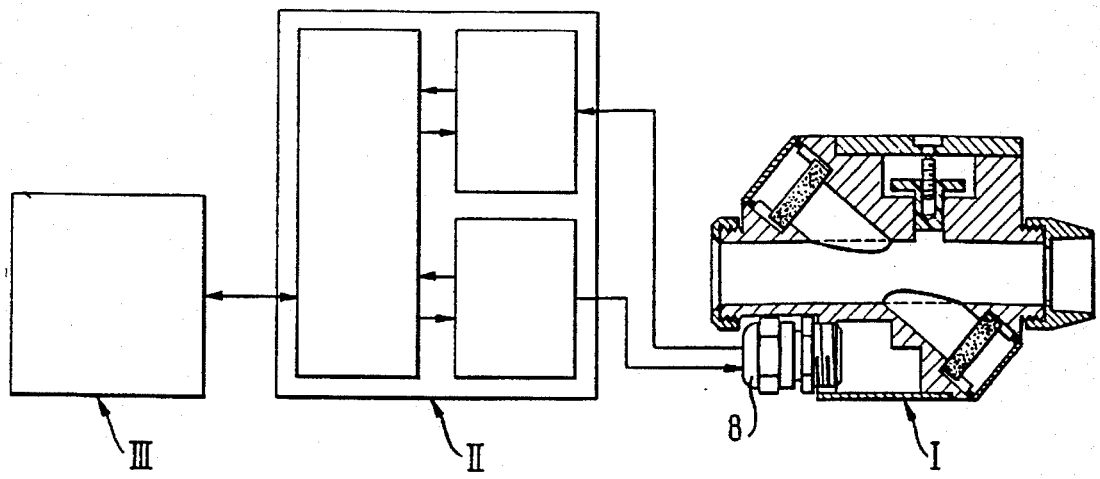
FIG. 1 is a block circuit diagram of a first embodiment of the invention.
Figure 2:
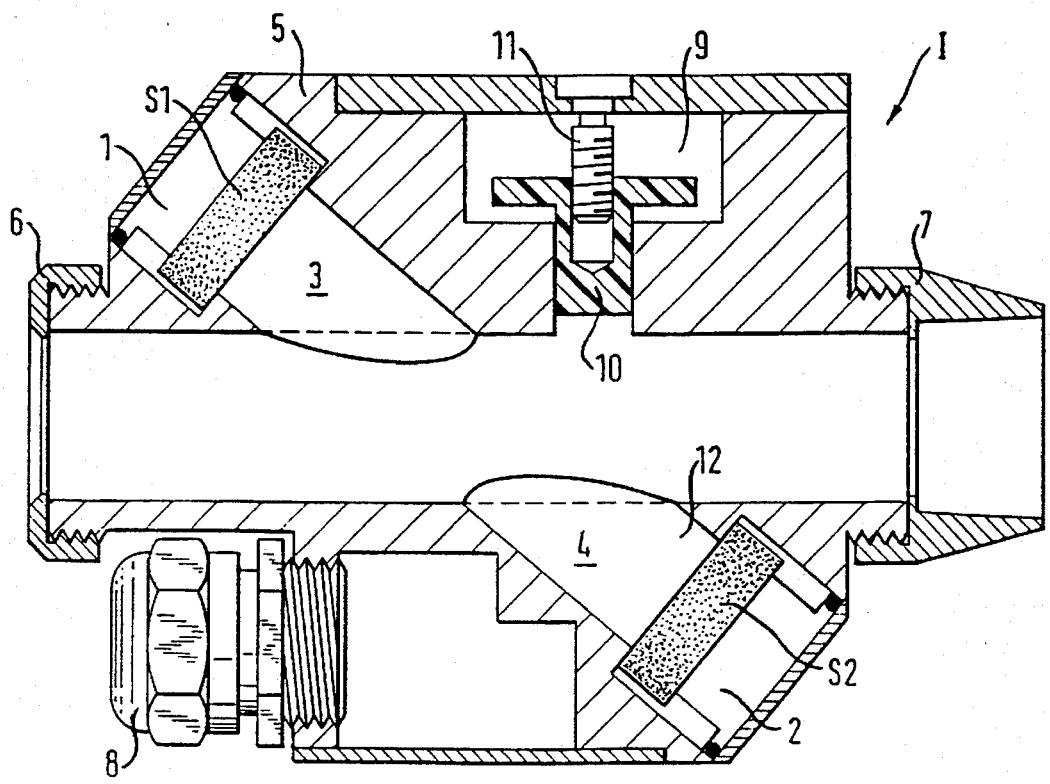
FIG. 2 is a diagrammatic sectional elevation of a part of the apparatus depicted in FIG. 1.

In FIG. 1 a block diagram is shown of the continuous flow measuring device for the determination of physiologically relevant pulmonary function parameters. A sensor head I is followed by a monitoring unit II and a data processing system III. In FIG. 2 the sensor head is indicated diagrammatically, which in the chambers 1 and 2 possesses ultrasonic transmit-receive elements S1 and S2. In this respect it is for instance a question of capacitor microphones, which are suitable both for transmitting and also for receiving ultrasonic signals. The cells S1 and S2, mounted obliquely in relation to a flow conducting tubular holder 5, transmit the sonic signal through the outlet apertures 3 and 4 to the opposite cell. Electrically insulating, lateral guide elements and also electrically insulating diffusors directed toward the holder 5 (in the form of gauze in the present embodiment), align the main cells in a fixed manner in the chambers 1 and 2. Connecting holes extend from these chambers to a pre-processing electronic system mounted to the side of the holder 5. This electronic system mainly serves for the amplification of the received signals and for signal conditioning of the temperature measurement points.

A cable, not illustrated in FIG. 2, and which emerges through a screw cable fitting 8 from the sensor head, connects the sensor with the associated monitoring unit II (see FIG. 1).

In the illustrated working embodiment of the invention the chamber 9 contains a device for lowering a thermoelement into the instrument duct 5. With the aid of a screw 11 an electrically non-conductive part 10, in which the thermoelement is set, is lowered into the holder 5. In the retracted position the holder may be cleaned with mechanical means without damage to the thermoelement.

A further thermoelement serves to determine the gas temperature in the chambers 3 and 4 upstream from the transmit-receive elements S1 and S2. It is positioned in the chamber 4 using a further lateral hole 12.

When the thermoelement holder 10 is lowered the holder 5 has a constant circular cross section along the entire length. The outlet apertures 3 and 4 are shut off by gauze so that in these parts as well the circular cross section of the tubular holder 5 will be maintained. To provide for improved cleaning or, respectively, sterilization of the holder 5 such gauze may be mounted on an interchangeable respiratory tube as well. For the instrument's duct two different, interchangeable connectors are available: the short version 6 serves to obtain a minimum sensor measuring volume, whereas the longer version 7 is so designed that an oral or adapter member may be inserted which is suitable for medical applications.

Additional heating elements, which serve to get the sensor head to a temperature higher than that of the surroundings, may be directly accommodated in the chambers provided for initial or pre-processing for electronics or in holes leading away from these chamber. A slight heating of the sensor offers the advantage that during the exhalation phase condensation of water vapor on the surfaces of the holder 5 may be prevented. In medical applications owing to the exhaled air's being saturated with water vapor heating of the sensor will be essential in most cases.

The manner of operation of the illustrated device will be explained with reference to FIG. 1. At the start of the measuring cycle the transmitter excites one of the transmit-receive cells S1 and S2 in alternate succession. An ultrasonic signal is output by the excited cell, which passes along the baseline to the opposite transmit-receive cell. The received signals amplified in the sensor itself pass back to the monitoring unit. Here the signal of the receiving transmit-receive cell is further amplified and supplied to an electronic circuit for the determination of the ultrasonic pulse transit time. It is in this manner that it is possible for electronic counters cascaded in a known manner to determine in sequence the ultrasonic transit time of S1 after S2 and of S2 after S1. The temperature signals necessary for the determination of the molar mass are also supplied to the monitoring unit after electronic pro-processing of the thermoelement signals in the sensor head itself. The mean gas temperature T arrived at using equations along the sonic transmission baseline is found as follows: it is assumed that the thermoelement introduced into the holder measures the mean temperature along the part of the baseline in the holder. The thermoelement positioned in the hole 12 to the side upstream from the cell S1 measures the mean temperature of the two parts of the baseline in the output apertures 3 and 4. In the embodiment described of the sensor head it is assumed as a simplification therefore that both the gas temperature and also the gas composition are the same in the two chambers 3 and 4. The mean gas temperature T is determined from the percentage fractions of the baseline, of the flow carrying and non-flow carrying sonic transmission baselines. The method includes performing temperature compensation measurements by determination of variations in gas temperature along the baseline using at least one temperature probe. Estimated temperatures for the temperature compensation measurements may be used as the estimated values may be based on physiological assumptions.

On the basis of the measured sonic transit time and the temperatures the processor of the monitoring unit calculates the molar mass, gas velocity and magnitudes derived therefrom. For calculation the equations set forth below are used.

The molar mass M may be determined using the equation:

$$M = k_1 \cdot k_A \cdot T \left( \frac{t_1 - t_2}{t_1 + t_2} \right)^2$$

wherein $k_1$ is a dimension-related constant, $k_A$ is a dimensionless constant for adiabatic exponent correction, T is a mean temperature along a baseline, and $t_1$ and $t_2$ represent transit times along the baseline reduced by time used for assembly and measurement.

The molar mass M may be derived using the equation:

$$M = k_2 \cdot k_a \cdot T \left( \frac{(t_1 - t_3)(t_2 - t_4)}{(t_1 + t_2 - t_3 - t_4)^2} \right)$$

wherein $k_2$ is a dimension-related constant, $k_A$ is a dimensionless constant for adiabatic exponent correction, T is a mean temperature along a baseline in a flow duct, determined using a temperature sensor positioned along said baseline, and $t_1$ and $t_2$ are transit times along the entire baseline reduced by time used for assembly and measurement, $t_3$ and $t_4$ are transit times reduced by time used for assembly and measurement, of the pulsed sonic signals along parts of the baseline not in the flow duct. Transit times $t_3$ and $t_4$ may be equal. Transit times $t_1$, $t_2$, $t_3$, and $t_4$ of the sonic pulses may be determined by electronic counting.

The magnitudes calculated by the processor of the monitoring unit may be transmitted to a computer via a serial interface. For the performance of physiological pulmonary function investigations such computer may perform further more elaborate calculations for the $CO_2$ and, respectively, $O_2$ concentration. In this case suitable sensors are employed in a fashion not described here to simultaneously determine the $CO_2$ fraction and/or the $O_2$ fraction in the respiratory air.

Accordingly one measuring cycle of the device comprises four phases: transmission of the sonic pulses, reception of the same at the opposite transmit-receive cell, processing of the data produced, data output and data transmission to the computer connected with the system. In the present embodiment of the apparatus such a measuring cycle will last approximately 3 ms. Since during a measuring cycle only one sonic transit time is measured, for the determination of a complete data set 2 to 4 measuring cycles are required dependent on the equation utilized. If the device is employed in pulmonary function diagnostics, the computer connected therewith may be used for the evaluation of the flow and molar mass data. With the aid of the computer it is possible for example for wash-out tests to be evaluated for the determination of the absolute lung volume.

Figure 3:
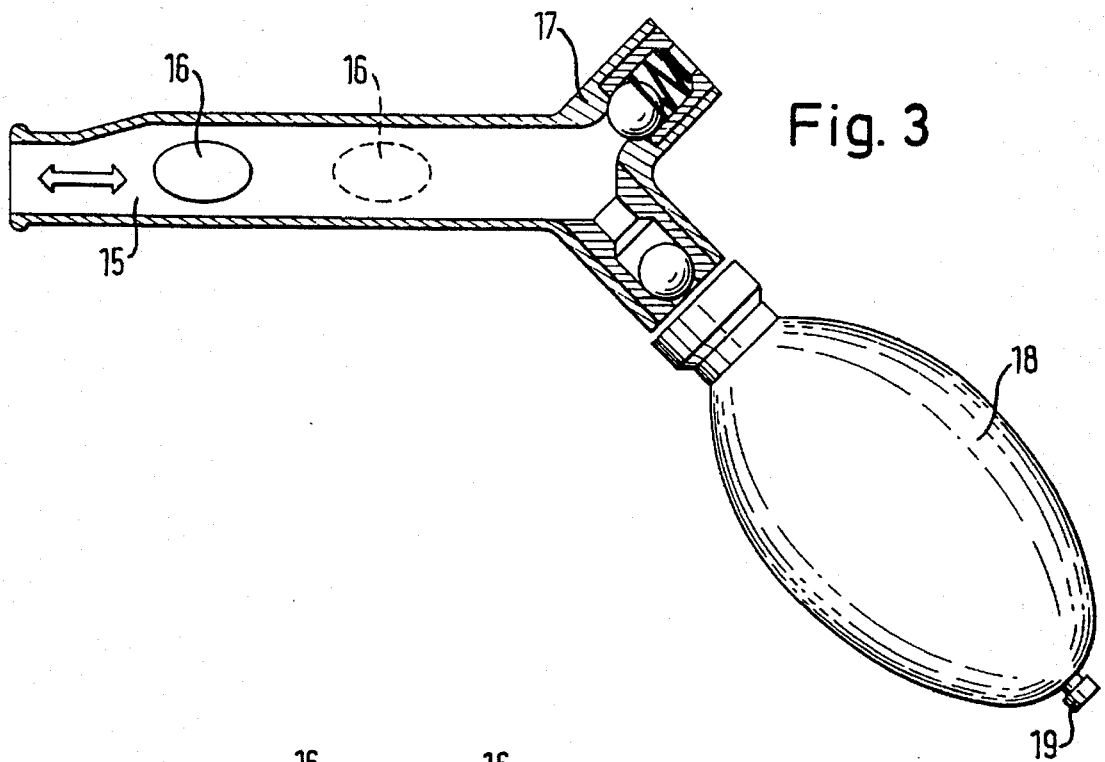
FIGS. 3 and 4 show various different embodiments of interchangeable respiratory tubes with branch members and gas containers able to be mounted thereon.
Figure 4:
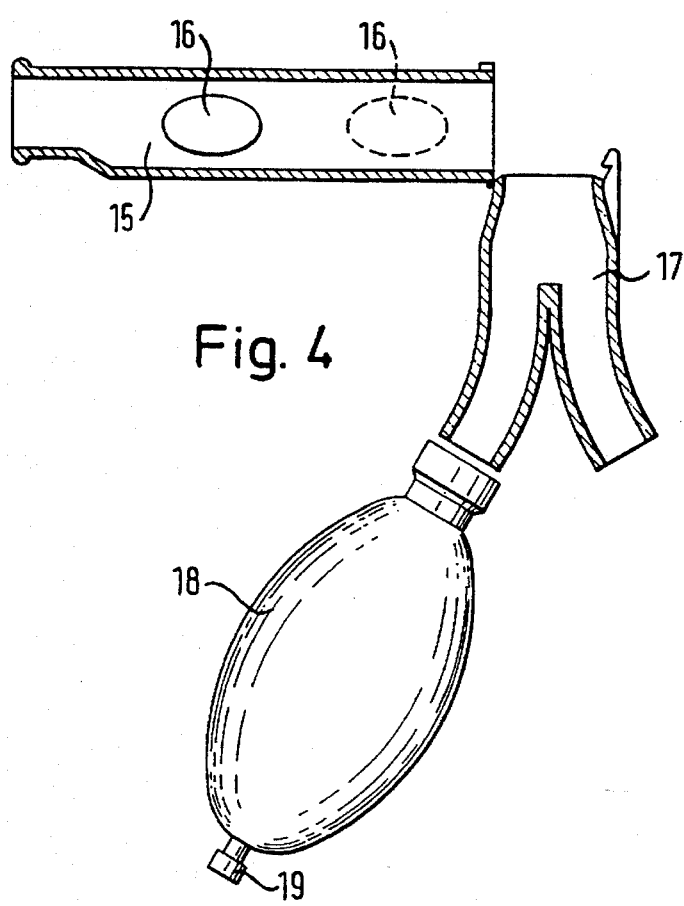

In FIGS. 3 and 4 components of the apparatus are illustrated, which are employed to ensure that the form of gas flow is regular. Reference numeral 15 indicates in FIGS. 3 and 4 the readily interchanged respiratory tube in each case, which is mounted in the holder 5. In the respiratory tube openings closed by suitable gauze or, respectively, diaphragms 16 are provided, such openings in the inserted condition of the respiratory tube assuming a position adjacent to the output aperture 3 and 4.

The branch part 17 assumes a position outside the respiratory tube 5. The embodiments in accordance with FIGS. 3 and 4 differ since in the embodiment of FIG. 3 the branch part 17 is designed to be integral with the internal tube 15. In the embodiment in accordance with FIG. 4 the branch part 17 is connected by means of a docking mechanism (not illustrated in detail) with the internal tube 15. On the branch part 17 a low-inertia bag 18, able to be filled with $O_2$ or a gas mixture, is mounted. This bag 18 possesses a charging port 19, adapted to be shut off by a valve, for filling the same with the respective gas or gas mixture. At its end, on which the bag 18 is mounted, the tube branch or, respectively, the branch part 17 has an inhalation valve (not illustrated). At the free tube end the branch part 17 possesses an exhalation valve.

Figure 5:
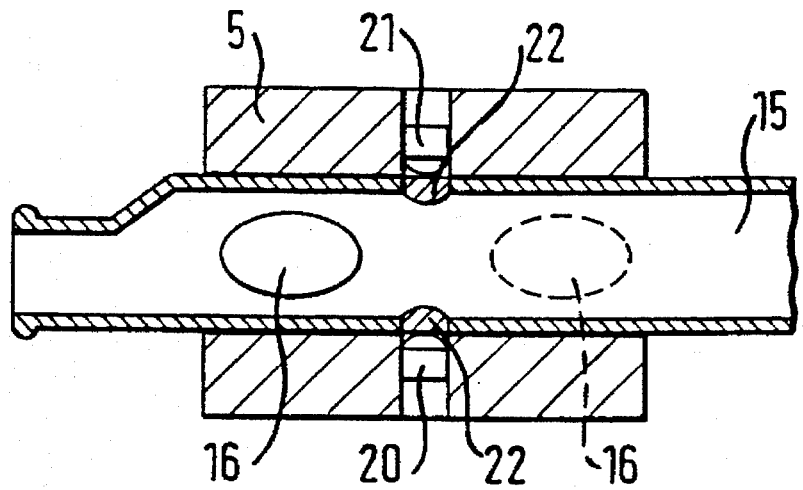
FIGS. 5 and 6 show diagrammatic sections of parts of the holder with additionally provided sensors and interchangeable respiratory tubes.

In the diagrammatic representation in accordance with FIG. 5 a white light or infrared light source 20 is integrated in the holder 5 in addition. Opposite to the same there is an infrared sensor 21. The readily interchanged respiratory tube 15 mounted in the holder possesses optically transparent windows 22 in the part opposite to the infrared light source or respectively the infrared sensor. Using the infrared sensor or, respectively, the infrared light source it is possible to measure the $CO_2$ content at the same time as flow measurement or, respectively, the molar mass.

Figure 6:
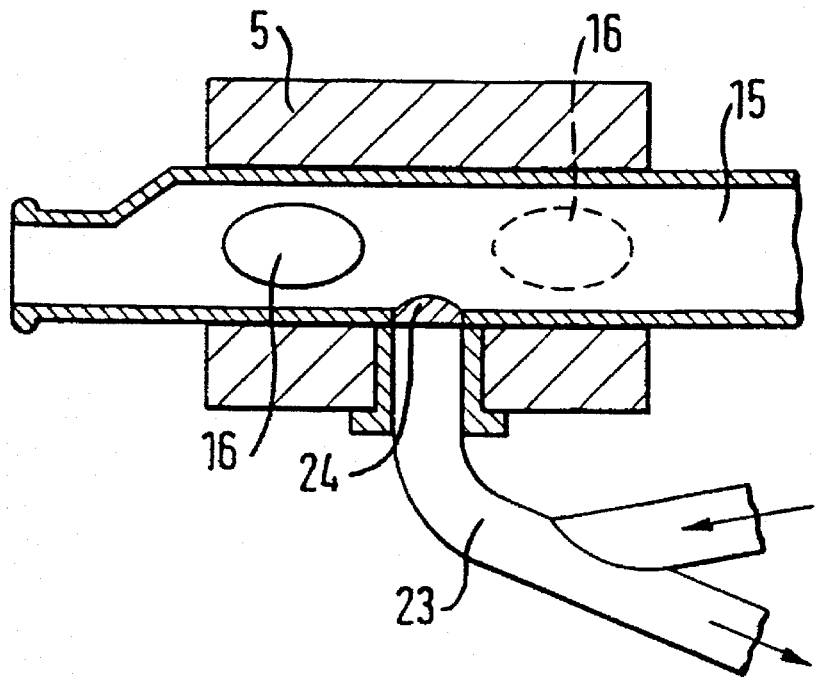

In the embodiment in accordance with FIG. 6 a glass fiber optic cable 23 is integrated in the holder, via which cable exciting light for $O_2$ analysis is introduced into the holder. On the other hand signal pulses received are passed on to a suitable sensor.

Adjacent to the opening of the optical glass fiber connection in the holder 5 the interchangeable respiratory tube possesses a thin, $O_2$ permeable but opaque diaphragm 24, on whose outer side an $O_2$ sensitive fluorescence indicator is applied. By means of this arrangement it is possible to measure the oxygen content in the sensor head ultrasonically simultaneously with the measurement of the flow and, respectively, molar mass.

In accordance with the present invention it is possible to use hygienic ultrasonic spirometry and a relatively simple gas analysis unit to perform an entire spiro-ergometry program. In comparison with previously known systems this has the great advantage that the measurements are performed on-line and in real time. Furthermore no moving parts are employed in the system, which might interfere with measurements. Accordingly extremely high accuracy and minimum possibilities of error are ensured.

We claim:

1. A method of measuring a molar mass of a gas or gas mixture, comprising:

flowing the gas or gas mixture through a holder on which one or more sonic or ultrasonic transmit and receive cells are arranged to define a baseline, wherein the sonic or ultrasonic transmit-receive cells radiate a pulsed sonic signal, measuring transit times of sonic pulses of the sonic signal along the baseline, performing temperature compensation measurements, and determining the molar mass from the transit times of the pulses of the sonic signal and the temperature compensation measurements, wherein the molar mass M is determined using the equation:

$$M = k_1 \cdot k_A \cdot T \left( \frac{t_1 - t_2}{t_1 + t_2} \right)^2$$

wherein $k_1$ is a dimension-related constant, $k_A$ is a dimensionless constant for adiabatic exponent correction, T is a mean temperature along the baseline, and $t_1$ and $t_2$ represent transit times along the baseline reduced by time used for assembly and measurement.

2. The method as claimed in claim 1, comprising performing said temperature compensation measurements by determination of variations in gas temperature along the baseline using at least one temperature probe.

3. The method as claimed in claim 1, comprising using estimated temperatures for said temperature compensation measurements.

4. The method as claimed in claim 1, wherein the transit times of the sonic pulses are also employed for computation of flow velocity of the gas or gas mixture.

5. The method as claimed in claim 1, wherein linearity errors of a flow velocity calculation are corrected by electrical circuits after the flow velocity calculation.

6. The method as claimed in claim 1, wherein for determination of diverse respiratory parameters the molar mass is employed for calculation of $CO_2$ and $O_2$ concentration variations of respiratory flow.

7. The method as claimed in claim 1, wherein measured molar mass values and measured flow-through values are employed as an initial basis for lung volume calculations and in that lung volume is determined by means of gas wash methods.

8. An apparatus for performance of the method of claim 1, wherein at least one sonic or ultrasonic transmit-receive cell pair is arranged obliquely to an axis of the holder and optionally at least one temperature probe is arranged along the baseline.

9. The apparatus as claimed in claim 8, wherein a baseline is integrated in the holder, which is set obliquely to a flow direction and having an aperture closed by sound transparent gauze or sound transmitting materials.

10. The apparatus as claimed in claim 8, comprising an interchangeable respiratory tube plugged into the holder.

11. The apparatus as claimed in claim 10, wherein the baseline is provided in a duct of the instrument, the duct is directly adjacent to the holder which is in the form of a tube, and the respiratory tube is arranged in the holder.

12. The apparatus as claimed in claim 11, wherein sensors, the instrument's duct and the respiratory tube are disposable parts.

13. The apparatus as claimed in claim 11, comprising damping elements to avoid interfering sonic reflections, and optionally a sound absorbing surface, integrally mounted on the holder or on the interchangeable respiratory tube.

14. An apparatus as claimed in claim 10, comprising a gas measuring sensor operated by an infrared sensor or by a fluorescence optical measurement system.

15. The apparatus as claimed in claim 14, wherein the respiratory tube is mounted in the holder and optically transparent windows are arranged adjacent positions at which a fluorescent light source or the infrared sensor are mounted in the holder.

16. The apparatus as claimed in claim 14, wherein the respiratory tube is mounted in the holder, and a window and a mirror opposite to the window are mounted in the holder.

17. The apparatus as claimed in claim 14, wherein the respiratory tube is mounted in the holder, and the respiratory tube contains an aperture, which is shut off by a thin $O_2$ permeable, opaque diaphragm, the holder further comprising a fluorescence indicator sensitive to $O_2$ on the outside of the respiratory tube.

18. The apparatus as claimed in claim 8 comprising elements at flow inlets and outlets for causing eddying of the gas or gas mixture flowing in and out.

19. The apparatus as claimed in claim 8, further comprising a thermostat for controlling the temperature within said holder.

20. The apparatus as claimed in claim 8, further comprising cavities for accommodating electronic circuit components.

21. An apparatus as claimed in claim 10, wherein a connecting adapter is mounted on the holder or on the respiratory tube, said adapter comprising a branch tube with a first end having a gas reservoir bag charged with $O_2$ or a gas mixture, and a free end wherein the first end of the branch tube further contains an inspiration valve and the free end of the branch tube contains an expiration valve.

22. The apparatus as claimed in claim 21, wherein the interchangeable respiratory tube comprises part of the branch tube.

23. The apparatus as claimed in claim 21, wherein with the valves inserted, the branch tube is connected with the holder or with the interchangeable respiratory tube.

24. The apparatus as claimed in claim 21, comprising a filling port on the gas reservoir bag for filling with entering gas.

25. The apparatus as claimed in claim 8, further comprising additional measuring apparatus for humidity measurement within the holder.

26. A method of measuring a molar mass of a gas or gas mixture, comprising flowing the gas or gas mixture through a holder on which one of more sonic or ultrasonic transmit and receive cells are arranged to define a baseline, wherein the sonic of ultrasonic transmit-receive cells radiate a pulsed sonic signal, measuring transit times of pulses of the sonic signal along a baseline, performing temperature compensation measurements and determining the molar mass from the transit times of the pulses of the sonic signal and the temperature compensation measurements, wherein the molar mass M is derived using the equation:

$$M = k_2 \cdot k_a \cdot T \left( \frac{(t_1 - t_3)(t_2 - t_4)}{(t_1 + t_2 - t_3 - t_4)^2} \right)$$

wherein $k_2$ is a dimension-related constant, $k_A$ is a dimensionless constant for adiabatic exponent correction, T is a mean temperature along a baseline in a flow duct, determined using a temperature sensor positioned along said baseline, and $t_1$ and $t_2$ are transit times along the baseline reduced by time used for assembly and measurement, $t_3$ and $t_4$ are transit times of the pulsed sonic signals, reduced by time used for assembly and measurements, along parts of the baseline not in the flow duct.

27. The method as claimed in claim 26, wherein $t_3$ and $t_4$ are equal.

28. The method as claimed in claim 26, wherein the transit times $t_1$, $t_2$, $t_3$ and $t_4$ of the sonic pulses are determined by electronic counting.

29. The method as claimed in claim 26 comprising performing said temperature compensation measurements by determination of variations in gas temperature along the baseline using at least one temperature probe.

* * * * *